United States Patent [19]

Chrisope

[11] Patent Number: 4,458,019

[45] Date of Patent: Jul. 3, 1984

[54] PORTABLE SYSTEM FOR ISOLATING AND CULTURING BACTERIUM AND DISPENSING A GASEOUS MIXTURE INTO CULTURE BAG AT LOCATION WHERE BACTERIUM IS OBTAINED

[76] Inventor: Gerald L. Chrisope, 309 Comanche St., Sulphur, La. 70663

[21] Appl. No.: 365,738

[22] Filed: Apr. 5, 1982

[51] Int. Cl.$^3$ .............................................. C12N 1/00
[52] U.S. Cl. .................................... 435/243; 435/30; 435/801; 435/810
[58] Field of Search ............... 435/287, 800, 810, 243, 435/30, 801

[56] References Cited

U.S. PATENT DOCUMENTS 3,948,733  4/1976  Conkerton ........................ 435/287
4,027,427  6/1977  Stoller et al. ................... 435/287 X Primary Examiner—Ferris H. Lander
Attorney, Agent, or Firm—Edwin E. Greigg

[57] ABSTRACT

This invention is directed to a method and system of obtaining a culture and placing the culture in a gaseous environment for transporting and incubating the culture. The method and system includes a fixed or portable small cylinder of a desired gaseous mixture, a nozzle secured to the outlet valve of the cylinder, a plurality of different sized zip-lock bags and a plurality of petri dishes or an equivalent type means for growing a culture.

1 Claim, 2 Drawing Figures

PORTABLE SYSTEM FOR ISOLATING AND CULTURING BACTERIUM AND DISPENSING A GASEOUS MIXTURE INTO CULTURE BAG AT LOCATION WHERE BACTERIUM IS OBTAINED

BACKGROUND OF THE INVENTION

This invention relates to a portable system for isolating and culturing bacterium and dispensing a gaseous mixture into a culture bag at the location at which the bacterium is obtained so that the culture bag can be transported to a test facility for incubation, or the gaseous mixture may be added at the culture center after the specimen has been received, or the specimen may be taken at the center and the gas added at the center.

Certain microorganisms require or prefer varying gas mixtures for optimal growth in in-vitro diagnostic environments. It is well known in the art that culture media in petri plates, vials, strips, etc., that certain microorganisms may be placed into a sealable plastic bag or vessel for culture under proper conditions. Provisions of the gas environment have been carried out by gas generating means which are placed into the bag with the growth sample and after sealing, the gas is released. Such systems have been set forth in U.S. Pat. Nos. 4,038,148 and 4,108,728. Such systems generate the gas in the bag after the bag has been sealed. Such systems must be controlled to prevent excess gases which would break the seal or bag. Other patents relating to petri dishes culture bags, etc. are as follows: U.S. Pat. Nos. 2,761,813; 3,591,461; 3,890,204; and 4,188,265.

The bacterium, *Campylobacter fetus* subspecies *jejuni*, has long been recognized as a pathogen causing abortion in cattle and swine. In recent years interest in this organism has increased throughout the world since it apparently is the etiologic agent for 3–11% of human patients with acute diarrhea. This level meets or exceeds that of Salmonella/Shigella outbreaks.

OBJECTS AND SUMMARY OF THE INVENTION

It is therefore an object of this invention to provide a portable kit or system for obtaining microorganisms and providing a gaseous environment for the microorganisms.

Another object is to provide a portable gas cylinder including a desired gaseous mixture suitable for providing an optimal gaseous atmosphere for cultivation of microorganisms.

Yet another object is to provide a method of cultivating microorganisms without the use of a vacuum means.

Other objects of the invention will become apparent from the following specification when considered with the drawings which illustrate features of the invention.

DESCRIPTION OF THE DRAWINGS

Figure 1:
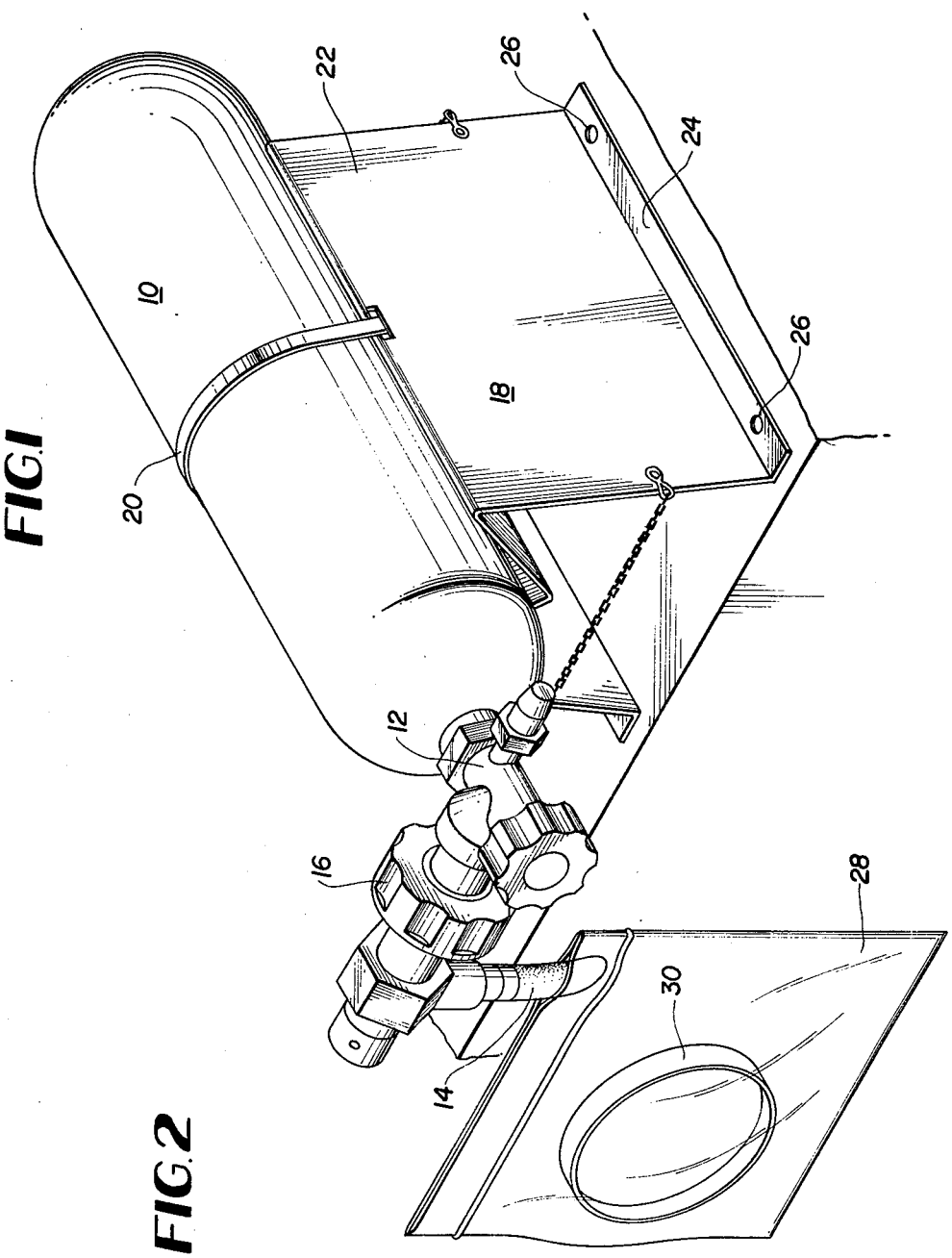
FIGS. 1 and 2 illustrate a portable gas cylinder in combination with a zip-lock bag illustrating a petri dish and a gas dispensing nozzle.
Figure 2:
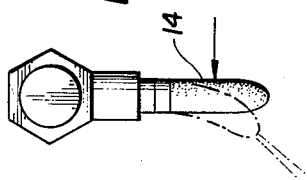

Now referring to the drawing, there is shown a portable gas tank or cylinder 10 including a control valve 12 for controlling the dispensing of gas from the cylinder. A dispensing nozzle 14 is secured to the main gas valve by any suitable means 16 so that gas can be dispensed from the cylinder through the nozzle into a sealable bag containing an inoculated plate or plates. The size of the bag depends upon the number of plates to be placed in the bag. The gas cylinder is supported on a V-stand 18 and is secured to the stand by a strap or spring means 20. The V-stand is provided with downwardly extending legs 22 each of which are provided with an outwardly extending edge 24 bent such that the edges 24 are parallel with a flat surface. The edges 24 are provided with apertures 26 so that the V-stand can be permanently secured to a flat surface such as a counter top by use of screws or bolts. If the stand is to be temporarily secured to the counter top, a C-clamp can be used on each leg edge 24 to secure the leg to the counter top. When used in a portable kit, a strap, small chain or some other means 28 may be secured from one leg to the other to prevent spreading of the legs due to the weight of the cylinder. In the latter case, the V-holder would rest upon any suitable surface.

The nozzle 14 is made of a semi-rigid material so that in its normal position the nozzle passage will be closed. The passage is opened by bending the nozzle; the greater the bend the greater the passage opening will become. The nozzle is assembled in a downward position and is secured to the cylinder valve outlet by threading the securing means by hand until it is tight. The nozzle securing means secures the nozzle in its downward position and holds the nozzle in the downward position.

The gas cylinder used in this invention is filled with a desired gaseous mixture suitable for forming the gaseous environment in which the innoculated plates are to be kept for bacteria growth. A Campy gas mixture of 5% $O_2$, 10% $CO_2$, and 85% N, may be used for capnophilic microorganisms such as Campylobacter.

A gaseous mixture of from 5–10% $H_2$, 10% $CO_2$, and 80–85% $N_2$ may be used for anaerobic microorganisms.

Another gaseous mixture may be 5–15% $CO_2$, Balance Air for Microorganisms which prefer an increased carbon dioxide tension, such as Streptococcus, Neisseria, Hemophilus, and Mycobacterium.

Gases such as the above are mixed and added to the gas cylinder under pressure for further use in incubating microorganisms in a Campy bag.

It will be obvious from the above description that one or more V-stands may be secured to a counter top for holding gas cylinders of different gases. The gas cylinders may be placed onto the V-stand when in use and stored elsewhere during non-use periods. The V-stand could be secured to the gas cylinder and placed in a kit along with petri dishes or other inoculation plates, etc. and a supply of sealable double-lock end bags for transporting a culture of microorganisms to an office or home are contained in the kit. Of course, the cylinder and V-stand could be separate and assembled when used. The cylinder is small and lightweight which makes it easily portable, and the V-stand may be used to hold the cylinder in its proper position for dispensing gas. The proper position is with the valve end of the cylinder placed such that the nozzle is down without any obstruction to placing a bag over the nozzle.

In operation, a specimen is obtained and smeared onto a petri dish to form a culture, the petri dish is placed into the bag and the bag is zipped almost closed. The bag is then filled with the proper gas by opening the cylinder valve, placing the nozzle into the bag, and bending the nozzle to permit gas to flow into the bag. Once the bag is filled, the nozzle is released and the nozzle closes off the gas flow. The nozzle is removed from the bag and the bag is squeezed by hand to force all the gas out of the bag. The outflow of gas clears the bag of any air or other contaminants. Once the bag is squeezed free of any gases, the nozzle is inserted into the bag a second time and the bag is again filled with gas by bending the nozzle to fill and releasing the nozzle to stop the gas flow. As the nozzle is removed from the bag, or the bag removed from the nozzle, by lowering the bag, the zip-lock is closed to retain the gas within the sealed bag. The valve of the cylinder is then closed. Make sure the bag is closed. The bag can then be transported to an incubator or wherever desired for culture growth.

Small bags can be used for one or two petri dishes or larger bags may be used for up to eight petri dishes. As set forth above, the gas cylinder, V-stand petri dishes and bags may be made into a kit for transporting to a home or an office at which place a specimen may be taken and then transported in a gaseous surrounding to any other place for incubation. It has been determined that zip-lock bags may be reused until they no longer remain firmly inflated for a time period of 48 hours subsequent to inflation.

The method set forth herein can be carried out without the use of an evacuating means for the bags and provides a system by which specimen may be obtained in a home and placed in an appropriate gaseous environment immediately after the specimen has been taken. In this manner the specimen will be protected during the time for transporting the culture to an incubator.

Some of the advantages of the present invention are: low cost, reusable bags, a ready available gas mixture, it is easy to operate and may be operated by skilled as well as unskilled persons, also it requires only a small space without a permanent hook-up.

The system has been described as being portable and useful in the home or office. Obviously any gas cylinder can be dangerous if not handled correctly. It is certainly safer to mount the V-stand to a counter top and then to secure the gas cylinder to the V-stand. Therefore, when it is possible, the gas cylinder should be secured to a holder which is permanently fixed in place. The position of the V-stand should be such that the gas cylinder can be secured with the valve end beyond the edge of the counter top with the nozzle down so that the culture bags may be easily slid up onto the nozzle without any obstruction.

The foregoing relates to preferred exemplary embodiments of the invention, it being understood that other embodiments and variants thereof are possible within the spirit and scope of the invention, the latter being defined by the appended claims.

What is claimed and desired to be secured by Letters Patent of the United States is:

1. A method of obtaining a culture of microorganisms and transporting said culture in a gaseous environment to an incubator station comprising:
   transporting a bacti gas kit containing a small gas cylinder containing a desired gaseous mixture, a plurality of sealable plastic bags, a plurality of culture media and a normally closed semi-rigid nozzle means for injecting said gaseous mixture into a sealable bag,
   obtaining a specimen of microörganisms,
   placing said specimen on a culture media,
   placing said culture media into a sealable plastic bag,
   partially closing the sealing bag,
   inserting one end of said normally closed semi-rigid nozzle means into said partially closed sealing bag,
   bending said nozzle means to permit gas flow thereby injecting said gaseous mixture into said sealable plastic bag containing said culture media,
   removing said nozzle means from said sealing bag,
   squeezing the plastic bag to squeeze out the gaseous mixture,
   again inserting said nozzle means into said partially closed sealing bag, bending said nozzle means and
   injecting said gaseous mixture into said bag thereby filling said bag with said gaseous mixture,
   sealing the bag, and
   transporting the bag to an incubator.

* * * * *